US008383554B2

(12) United States Patent
Wong et al.

(10) Patent No.: US 8,383,554 B2
(45) Date of Patent: Feb. 26, 2013

(54) QUANTITATIVE MICROARRAY OF INTACT GLYCOLIPID CD1D INTERACTION AND CORRELATION WITH CELL-BASED CYTOKINE PRODUCTION

(75) Inventors: Chi-Huey Wong, La Jolla, CA (US); Pi-Hui Liang, Taipei (TW)

(73) Assignee: Academia Sinica, Taipei (TW)

( * ) Notice: Subject to any disclaimer, the term of this patent is extended or adjusted under 35 U.S.C. 154(b) by 457 days.

(21) Appl. No.: 12/423,728

(22) Filed: Apr. 14, 2009

(65) Prior Publication Data

US 2009/0275483 A1 Nov. 5, 2009

Related U.S. Application Data

(60) Provisional application No. 61/044,867, filed on Apr. 14, 2008.

(51) Int. Cl.
*C40B 60/00* (2006.01)
*C40B 40/12* (2006.01)
*C07G 3/00* (2006.01)
(52) U.S. Cl. .............................. 506/33; 506/19; 536/4.1
(58) Field of Classification Search ........................ None
See application file for complete search history.

(56) References Cited

U.S. PATENT DOCUMENTS

2006/0264382 A1* 11/2006 Savage et al. ................... 514/23
2007/0059769 A1* 3/2007 Blixt et al. ..................... 435/7.1

OTHER PUBLICATIONS

Shin et al., "Carbohydrate Microarrays: An Advanced Technology for Functional Studies of Glycans" 2005, Chemistry: A European Journal, pp. 2894-2901.*
Bryan et al., Covalent Display of Oligosaccharide Arrays in Microtiter Plates, 2004, JACS, 126, 8640-8641.*
Zeng, Z.; Castano, A. R.; Segelke, B. W.; Stura, E. A.; Peterson, P. A.; Wilson, I. A. Science 1997, 277, 339-345.
Brgl, M.; Brenner, M. B. Annu. Rev. Immunol. 2004, 22, 817-890.
Porcelli, S. A.; Modlin, R. L. Annu. Rev. Immunol. 1999, 17, 297-329.
Jayawardena-Wolf, J.; Bendelac, A. Curr. Opin. Immunol. 2001, 13, 109-113.
Tsuji, M. Cell. Mol. Life Sci. 2006, 63, 1889-1898.
Hong, S.; Wilson, M. T.; Serizawa, I.; Wu, L.; Singh, N.; Naidenko, O. V.; Miura, T.; Haba, T.; Scherer, D. C.; Wei, J.; Kronenberg, M.; Koezuka, Y.; Van Kaer, L. Nat. Med. 2001, 7, 1052-1056.
Burdin, N.; Brossay, L.; Kronenberg, M. Eur. J. Immunol. 1999, 29, 2014-2025.
Kronenberg, M.; Gapin, L. Nat. Rev. Immunol. 2002, 8, 557-568.
Brossay, L.; Chioda, M.; Burdin, N.; Koezuka, Y.; Casorati, G.; Dellabona, P.; Kronenberg, M. J. Exp. Med. 1998, 188, 1521-1528.
Taniguchi , M.; Harada, M.; Kojo, S.; Nakayama, T.; Wakao, H. Annu. Rev. Immunol. 2003, 21, 483-513.
Gonzalez-Aseguinolaza G.; Van Kaer L.; Bergmann C. C.; Wilson J. M.; Schmieg J.; Kronenberg, M.; Nakayama, T.; Taniguchi, M.; Koezuka, Y.; Tsuji, M. J. Exp. Med. 2002, 195, 617-624.
Chang, Y.-J.; Huang, J.-R.; Tsai, Y.-C.; Hung, J.-T.; Wu, D.; Fujio, M.; Wong, C.-H.; Yu, A. L. Proc. Natl. Acad. Sci. U.S A. 2007, 104, 10299-10304.
Giaccone, G. ; Punt, C. J.; Ando, Y.; Ruijter, R.; Nishi, N.; Peters, M.; von Blomberg, B. M.; Scheper, R. J.; van der Vliet, H. J.; van den Eertwegh, A. J.; Roelvink, M.; Beijnen, J.; Zwierzina, H.; Pinedo, H. M. Clin. Cancer Res. 2002, 8, 3702-3709.
Smyth, M. J.; Godfrey, D. I. Nat. Immunol. 2000, 1, 459-460.
Berkers, C. R.; Ov aa, H. Trends Pharmacol. Sci. 2005, 26, 252-257.
Yu, K. O.; Im, J. S.; Molano, A.; Dutronc, Y.; Illarionov, P. A.; Forestier, C.; Fujiwara, N.; Arias, I.; Miyake, S.; Yamamura, T.; Chang, Y. T.; Besra, G. S.; Porcelli, S. A. Proc. Natl. Acad. Sci. U.S.A. 2005, 102, 3383-3388.
Yang, G.; Schmieg, J.; Tusji, M.; Franck, R. W. Angew. Chem. Int. Ed. 2004, 43, 3818-3822.
Fujio, M .; Wu, D.; Garcia-Navarro, R.; Ho, D. D.; Tsuji, M.; Wong, C.-H. J. Am. Chem. Soc., 2006, 128, 9022-9023.
Naidenko, O. V.; Maher, J. K.; Ernst, W. A.; Sakai, T.; Modlin, R. L.; Kronenberg, M. J. Exp. Med. 1999, 190, 1069-1080.
Cantu III, C.; Benlagha, K.; Savage, P. B. ; Bendelac, A.; Teyton, L. J. Immunol. 2003, 4673-4682.
Im, J. S.; Yu, K. O. A.; Illarionov, P. A.; LeClair, K. P.; Storey, J. R.; Kennedy, M. W.; Besra, G. S.; Porcelli, S. A. J. Biol. Chem. 2004, 279, 299-310.
Willats, W. G.; Rasmussen, S. E.; Kristensen, T.; Mikkelsen, J. D.; Knox, J. P. Proteomics 2002, 2, 1666-1671.
Wang, D.; Liu, S.; Trummer, B. J.; Deng, C.; Wang, A. Nat. Biotechnol. 2002, 20, 275-281.
Feizi, T., Mulloy, B. Curr. Opin. Struct. Biol. 2003, 13, 602-604.
Feizi, T., Fazio, F., Chai, W., Wong, C.-H. Curr. Opin. Struct. Biol. 2003, 13, 637-645.
Liang, P.-H.; Wang, S.-K. Wong, C.-H. J. Am. Chem. Soc. 2007, 129, 11177-11184.
Zajonc, D. M .; Maricic, I.; Wu, D.; Halder, R.; Roy, K.; Wong, C.-H.; Kumar, V.; Wilson, I. A. J. Exp. Med. 2005, 202, 1517-1526.

(Continued)

*Primary Examiner* — Amber D Steele
*Assistant Examiner* — Lianko Garyu
(74) *Attorney, Agent, or Firm* — Shantanu Basu; Eckman Basu LLP (57) ABSTRACT

The protein CD1d binds self and foreign glycolipids for presentation to CD1-restricted T cells by means of TCR recognition, and activates $T_H1$ and $T_H2$ chemokines release. Accordingly, a variety of glycolipid ligands were attached to a microarray surface and their binding with CD1d investigated. An α-galactosyl ceramide (α-GalCer) bearing a carbamate group at the 6'-OH position was tethered to the surface and the dissociation constant with CD1d determined. Competition assays were used to determine the dissociation constants ($K_i$) of the new and intact glycolipids. The para-fluoroheptaphenyl-modified α-GalCer was found to bind most strongly with CD1d ($K_i$ 0.14 µM), two orders of magnitude stronger than α-GalCer and more than three times more selective for IFN-γ release. Various α-GalCer analogs were analyzed and the results showed that the binding affinity of glycolipids to CD1d correlates well with IFN-γ production, but poorly with IL-4 secretion by NKT cells, suggesting that tighter binding ligands could bias cytokine release through the $T_H1$ pathway.

6 Claims, 11 Drawing Sheets

OTHER PUBLICATIONS

Koch, M.; Stronge, V. S.; Shepherd, D.; Gadola, S. D.; Mathew, B.; Ritter, G.; Fersht, A. R.; Besra, G. S.; Schmidt, R. R.; Jones, E. Y.; Cerundolo, V. Nat. Immunol. 2005, 6, 819-826.

Zajonc, D. M.; Cantu, III, C.; Mattner, J.; Zhou, D.; Savage, P. B.; Bendelac, A.; Wilson, I. A.; Teyton, L. Nat. Immunol. 2005, 6, 810-818.

Borg, N. A.; Wun, K. S.; Kjer-Nielsen, L.; Wilce, M. C.; Pellicci, D. G.; Koh, R.; Besra, G. S.; Bharadwaj, M.; Godfrey, D. I.; McCluskey, J.; Rossjohn, J. Nature 2007, 488, 44-49.

Kanter, J. L.; Narayana, S.; Ho, P. P.; Catz, I.; Warren, K. G.; Sobel, R. A.; Steinman, L.; Robinson, W. H. Nature Med. 2006, 12, 138-143.

Spada, F. M.; Koezuka, Y.; Porcelli, S. A. J. Exp. Med. 1998, 188, 1529-1534.

Gumperz. J. E.; Roy, C.; Makowska, A.; Lum, D.; Sugita, M.; Podrebarac, T.; Koezuka, Y.; Porcelli, S. A.; Cardell, S.; Brenner, M. B.; Behar, S. M. Immunity, 2000, 12, 211-221.

Kang, S. J.; Cresswell P. Nat. Immunol 2004, 5, 175-181.

Yuan, W.; Qi, X.; Tsang, P.; Kang, S. J.; Illarionov, P. A.; Besra, G. S.; Gumperz, J.; Cresswell, P. Proc. Natl. Acad. Sci. U.S.A 2007, 104, 5551-5556.

Mammen M.; Choi, S.-K. Whitesides, G. M. Angew. Chem. Int. Ed. 1998, 37, 2754-2794.

Oki, S.; Chiba, A.; Yamamura, T.; Miyake, S. J. Clin. Invest. 2004, 113, 1631-1640.

Tanaka S.; Tsu kada, J.; Suzuki, W.; Hayashi, K.; Tanigaki, K.; Tsuji, M.; Inoue, H.; Honjo, T.; Kubo, M. Immunity 2006, 24, 689-701.

Calabi, F.; Jarvis, J. M.; Martin, L.; Milstein, C. Eur. J. Immunol. 1989, 19, 285-292.

Singh, N.; Hong, S.; Scherer, D. C.; Serizawa, I.; Burdin, N.; Kronenberg, M.; Koezuka, Y.; Van Kaer, L. J. Immunol. 1999, 163, 2373-2377.

Goff, R. D.; Gao, Y.; Mattner, J.; Zhou, D.; Yin, N.; Cantu, III, C.; Teyton, L.; Bendelac, A..; Savage, P. B. J. Am. Chem. Soc. 2004, 126, 13602-13603.

Mong, K.-K. T.; Wong, C.-H. Angew. Chem. Int. Ed. 2002, 41, 4087-4090.

Wu, D.; Xing, G..-W.; Poles, M. A.; Horowitz, A.; Kinjo, Y.; Sullivan, B.; Bodmer-Narkevitch, V.; Plettenburg, O.; Kronenberg, M.; Tsuji, M.; Ho, D. D.; Wong, C.-H. Proc. Natl. Acad. Sci. U.S.A. 2005. 102. 1351-1356.

Schmieg, J.; Yang, G.; Franck, R. W.; Tsuji, M. J. Exp. Med. 2003, 198, 1631-1641.

Hirabayashi, J. Trends Biotechnol. 2003, 21, 141-143.

\* cited by examiner

| Compd | Structure | Microarray $K_i$ (μM)[1] | NKT cell cytokine secretion IFN-γ secretion[2] | IL-4 secretion[2] | IFN-γ/IL-4 ratio[3] |
|---|---|---|---|---|---|
| α-GalCer | R=((CH$_2$)$_{24}$CH$_3$ | 14 ± 1.5 | 1.00 | 1.00 | 1.00 |
| 11 | R=(CH$_2$)$_5$Ph | 2.3 ± 1.4 | 1.12 ± 0.08 | 0.73 ± 0.16 | 1.53 ± 0.15 |
| 12 | R=(CH$_2$)$_6$Ph | 1.7 ± 1.1 | 1.28 ± 0.08 | 0.74 ± 0.16 | 1.73 ± 0.17 |
| 13 | R=(CH$_2$)$_7$Ph | 1.5 ± 0.4 | 1.80 ± 0.15 | 0.87 ± 0.27 | 2.07 ± 0.26 |
| 14 | R=(CH$_2$)$_8$Ph | 2.5 ± 0.05 | 1.56 ± 0.11 | 0.72 ± 0.19 | 2.17 ± 0.24 |
| 15 | R=(CH$_2$)$_9$Ph | 6.3 ± 2.2 | 0.86 ± 0.06 | 0.59 ± 0.15 | 1.46 ± 0.15 |
| 16 | R=(CH$_2$)$_{10}$Ph | 1.7 ± 0.6 | 1.22 ± 0.08 | 0.87 ± 0.28 | 1.40 ± 0.15 |
| 17 | R=(CH$_2$)$_{14}$Ph | 17 ± 5.1 | 0.17 ± 0.01 | 0.71 ± 0.10 | 0.24 ± 0.03 |
| 18 | R=(CH$_2$)$_7$Ph(p-F) | 0.14 ± 0.02 | 2.39 ± 0.13 | 0.80 ± 0.09 | 3.00 ± 0.16 |
| 19 | R=(CH$_2$)$_7$Ph(p-OMe) | 0.28 ± 0.13 | 2.25 ± 0.06 | 0.79 ± 0.06 | 2.85 ± 0.10 |
| 20 | R=(CH$_2$)$_7$Ph(p-CF$_3$) | 1.2 ± 0.6 | 1.43 ± 0.07 | 0.76 ± 0.08 | 1.88 ± 0.08 |
| 21 | R=(CH$_2$)$_7$Ph(p-Ph) | 13 ± 4.8 | 0.17 ± 0.003 | 0.56 ± 0.04 | 0.30 ± 0.01 |
| 22 | R=(CH$_2$)$_{10}$Ph(p-F) | 0.46 ± 0.12 | 2.13 ± 0.003 | 0.81 ± 0.13 | 2.62 ± 0.18 |
| 23 | R=(CH$_2$)$_{10}$Ph(p-OMe) | 0.33 ± 0.09 | 1.91 ± 0.19 | 0.87 ± 0.07 | 2.19 ± 0.12 |
| 24 | R=(CH$_2$)$_{10}$Ph(p-CF$_3$) | 4.2 ± 1.26 | 1.65 ± 0.20 | 0.87 ± 0.21 | 1.89 ± 0.22 |
| 25 | R=(CH$_2$)$_{10}$Ph(p-Ph) | >100 | 0.33 ± 0.001 | 0.61 ± 0.06 | 0.55 ± 0.04 |
| 26 | - | 36 ± 8.9 | 0.12 ± 0.006 | 0.59 ± 0.15 | 0.20 ± 0.02 |

[1] All the experiments were performed in triplicates, and the data are presented as mean ± SD. [2] The values were obtained from the cytokine (IFN-γ and IL-4) productions of glycolipids normalized to the cytokine productions of α-GalCer. [3] The ratios were obtained from IFN-γ ratio/ IL-4 ratio.

QUANTITATIVE MICROARRAY OF INTACT GLYCOLIPID CD1D INTERACTION AND CORRELATION WITH CELL-BASED CYTOKINE PRODUCTION

RELATED APPLICATIONS

This application claims the benefit of and priority to U.S. Provisional Application Ser. No. 61/044,867, filed Apr. 14, 2008, the contents of which are incorporated by reference herein in their entirety.

FIELD OF DISCLOSURE

This disclosure relates to sensitive, high throughput, glycan microarray systems, methods and devices for examining carbohydrate-protein interactions on surface and in solution. More particularly, the glycan microarray is a platform for using very small amounts of materials. The glycan microarray supports multivalent interactions and may be used to determine the surface dissociation constant ($K_{D, \, surf}$).

SUMMARY

The protein CD1d binds self and foreign glycolipids for presentation to CD1-restricted T cells by means of TCR recognition, and activates $T_H1$ and $T_H2$ chemokines release. A variety of glycolipid ligands were attached to a microarray surface and their binding with CD1d investigated. α-galactosyl ceramide (α-GalCer) bearing a carbamate group at the 6'-OH position were tethered to the surface and the dissociation constant with CD1d determined. Competition assays were used to determine the dissociation constants ($K_i$) of the new and intact glycolipids. The para-fluoroheptaphenyl-modified α-GalCer was found to bind most strongly with CD1d ($K_i$ 0.14 µM), two orders of magnitude stronger than α-GalCer and more than three times more selective for IFN-γ release. Various α-GalCer analogs were analyzed and the results showed that the binding affinity of glycolipids to CD1d correlates well with IFN-γ production, but poorly with IL-4 secretion by NKT cells, suggesting that tighter binding ligands could bias cytokine release through the $T_H1$ pathway.

According to features of the present disclosure, a method is disclosed comprising binding α-GalCer or αGalCer derivatives to a substrate to form a microarray, incubating the microarray with CD1 molecules; and taking measurements to determine binding of the CD1 molecules to the α-GalCer or α-GalCer derivatives.

According to features of the present disclosure, a device is disclosed comprising a plurality of glycan ligands bound to a substrate, wherein substantially all of the glycan ligands are orientated such that the carbohydrate portion of the glycan is oriented substantially closest to the substrate in what could be called a "head down" orientation. According to implementations, the glycan of a device may be modified at the 6' position with an R group, R is $CHR_1$—X—Y, where $R_1$ is an organic moiety such as amide, carbamate, carbonate, or urea; X is alkyl, alkoxyl, or aryl-alkyl; and Y is $NH_2$, COOH, $N_3$, alkyne, or biotin.

All scientific terms are to be given their ordinary meanings as understood by those of skill in the art, unless an alternate meaning is set forth below. In case of conflict, the definitions set forth in this specification shall control.

DRAWINGS

The above-mentioned features and objects of the present disclosure will become more apparent with reference to the following description taken in conjunction with the accompanying drawings wherein like reference numerals denote like elements and in which:

FIG. 2 illustrates exemplary implementations of: (a) array fabrication and detection. The glycolipid was printed onto the slide and its presence detected using recombinant dimeric CD1d protein. The spot image was generated from the pre-complex of biotin-anti-mCD1d antibody and $Cy_3$ labeled streptavidin; (b) the images from the array scanner, every derivatives (1-4) were printed on the slide from 1000 (right-most column), 800, 600, 400, 200, 100, 80, 60, 40, 20, 10, 8, 6, 4, 2, 1, 0.8, 0.6, 0.4, 0.2 µM (left-most column) and incubated with CD1d; the arrow indicates the limit of detection for compound 1 (1 µM). The bar indicates 1 mm in length;

FIG. 3 illustrates exemplary implementations as follows (a) Compound 1 was printed with concentrations of 1000 (left-most column), 900, 800, 700, 600, 500, 400, 300, 200, 100, 80, 60, 40, 20, 10, 5 µM (right-most column); the images were obtained from the slides after incubation with different concentrations of CD1d (from 800 nM to 6.25 nM as indicated above each square) followed by detection of a pre-complex of biotin labeled anti-CD1d and $Cy_3$-labelled streptavidin; (b) binding curves for compound 1 printed at different concentrations are shown; and (c) the $K_{D, \, surf}$ values vs printing concentrations were obtained (higher printing concentration gave a tighter binding);

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

According to exemplary implementations, analysis using microarrays comprising glycolipids attached to slides is performed with the following procedure:

1. 0.7 nl of amine-containing glycans (50 µM in printing buffer) were printed by robotic pin onto NHS-coated glass slides;
2. Printed slides were allowed to react in an atmosphere of 80% humidity for an hour followed by desiccation overnight. These slides were stored at room temperature in a desiccator until use;
3. Before the assay, these slides were blocked with 100 µl blocking buffer for 30 minutes;
4. Wash twice with 100 µl PBST;
5. Add 50 µl of diluted primary antibody and incubate at room temperature for 1 hour;
6. Wash 3 times with 100 µl PBST;
7. Pipet 50 µl of secondary antibody solution (1:200) and incubate at room temperature for approximately 45 minutes;
8. Wash 3 times with 100 µl PBST;
9. Wash with water and air dry; and
10. Data Analysis.

Specifically disclosed herein is an α-GalCer array (with the sugar portion affixed to the array) having a modification at 6' position. Accordingly, α-GalCer molecule comprises an exemplary implementation of the α-GalCer molecules that form the array:

Formula 1 where R is $CHR_1$—X—Y, $R_1$ is an organic moiety such as amide, carbamate, carbonate, urea, etc.; X is alkyl, alkoxyl, aryl-alkyl, etc.; and Y is $NH_2$, COOH, $N_3$, alkyne, biotin, etc.

According to another aspect, one or more kits of parts can be envisioned by the person skilled in the art, the kits of parts to perform at least one of the methods herein disclosed, the kit of parts comprising one or more microarray devices, the devices comprising a plurality of glycan ligands bound to a substrate; wherein substantially all of the glycan ligands are orientated such that the carbohydrate portion of the glycan is oriented substantially closest to the substrate; wherein the glycan ligands are α-GalCer or α-GalCer derivatives. The kits possibly include devices for reading, operating, interpreting, or processing data produced by the one or more microarrays, as well as instructions for use of the kit and its constituent parts.

The interaction between a glycolipid and the protein CD1d has been analyzed using a microarray-based method. The 6'-OH derivative of α-GalCer was covalently bound to a glass surface, and shown to have $K_{D, surf}$ of 100 to 500 nM with recombinant dimeric mCD1d at a variety of different printing concentrations. The binding was found to be stronger at higher surface densities. The solution dissociation constants ($K_i$) of intact α-GalCer and its derivatives were obtained by performing competitive binding experiments. The para-F derivative 18 was found to bind most strongly to CD1d with a $K_i$ of 0.14 µM, two orders of magnitude higher than α-GalCer, and induce the most IFN-γ secretions. Using various α-GalCer analogs, the binding affinity of glycolipids to CD1d was found to correlate well with IFN-γ production by NKT cells, but less so with IL-4 secretion, consistent with assumptions that tighter binding compounds could bias cytokine release through the $T_H1$ pathway. This microarray method should facilitate the analysis of lipid binding and constitutes a relatively simple in vitro system for probing the physiological function of proteins and elucidating their potential role in the immune response.

Although specific reference to glycolipids is presented herein, artisans will readily understand that the principles disclosed herein have specific reference to glycans generally. Therefore, it is specifically contemplated that where glycolipids are disclosed, glycans generally may be substituted depending on the objectives or aims of a given set of experiments without undue experimentation.

Figure 1:
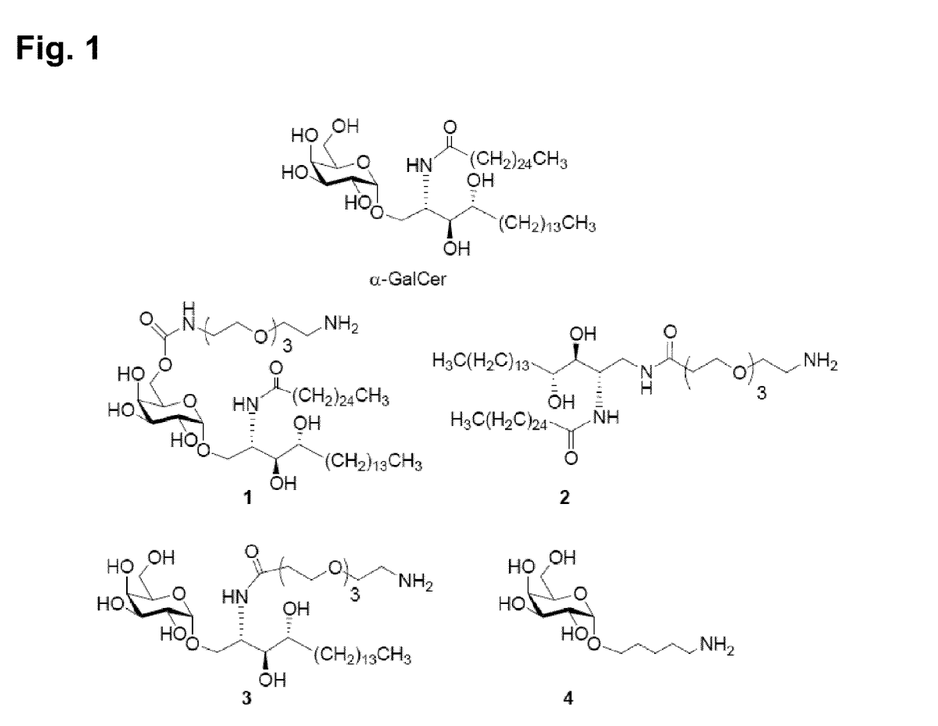
FIG. 1 shows implementations of α-GalCer and its derivatives 1-4.

CD1 molecules are heterodimers, composed of a heavy polypeptide chain non-covalently associated with a 2-microglobulin, and have substantial structural similarity to major histocompatibility complex (MHC) class I proteins. There are four members of the CD1 family, denoted group I (CD1a, b, c and e) and group II (CD1d) on the basis of sequence identity and chromosomal location. Each CD1 mediates T-cell responses through the presentation of self and foreign lipids, glycolipids, lipopeptides, or amphipathic small molecules to T-cell receptors (TCR).

α-GalCer (FIG. 1), a glycolipid found in the marine sponge Agelas mauritianus, is the most extensively studied ligand for CD1d. When bound to CD1d, α-GalCer stimulates rapid $T_H1$ (such as IFN-γ) and $T_H2$ (IL-4) cytokine production by Vα14i natural killer T (Vα14i NKT) cells in mice and the human homologue Vα24i NKT cells by means of TCR recognition. The production of $T_H1$ cytokines is thought to be responsible for the anti-tumor, anti-viral/bacterial/parasitic, and adjuvant effects of α-GalCer, while $T_H2$ cytokines production is thought to correlate with the amelioration of certain autoimmune diseases (e.g. type 1 diabetes and multiple sclerosis). α-GalCer has been the subject of several clinical trials for its anti-cancer potential but was found to be ineffective, possibly because the therapeutic effects of IFN-γ were hindered by IL-4. Therefore, compounds which increase the selectivity toward either the $T_H1$ or $T_H2$ cytokines response may be more therapeutically useful.

Amongst the factors that could cause a cytokine profile shift, the stability of CD1d/glycolipid complex may play a significant role. A less stable association between the glycolipid and CD1d, for example, could result in a shorter half-life for NKT cell stimulation. For IFN-γ production to occur, a longer TCR stimulation is required. IL-4 production occurs after only 2 h of stimulation, while IFN-γ production by NKT cells requires an initial stimulation period at least 1-2 h longer. Thus, improving the stability of the α-GalCer/CD1d complex could potentially enhance the $T_H1$ response by prolonging stimulation of NKT cells. The first α-GalCer analogue known to enhance $T_H1$ response is a stable C-glycoside analogue (α-C-GalCer), through its binding affinity to CD1d is relatively low. A series of glycolipids bearing aromatic groups on the acyl side chain have been synthesized and these molecules were found to skew the cytokine release profile towards a $T_H1$ response.

While the designed glycolipids were evaluated by functional assay, examination of the binding affinity between these glycolipids and CD1d was less easily addressed. Progress towards an understanding of the binding properties between glycolipids and CD1d has been slow. A major problem is the lack of method for measuring the binding constant of intact glycolipid. In addition, the physical properties of lipids, e.g. critical micelle concentration (CMC) and solubility, or the slow association and dissociation of binding may make the study difficult. Because lipid antigens presented by CD1d molecules can trigger and regulate a wide variety of immune responses, a sensitive, accurate, and reproducible high-throughput assay to probe the antigen binding properties to CD1d would be very useful. Several previous studies have examined the lipid binding properties of CD1d, using surface plasmon resonance (SPR), isoelectric focusing (IEF), and isothermal calorimetry (ITC). The SPR method suffered from low signal to noise ratio and the ITC assay required a large amount of protein for each assay. The utility of fluorescent lipid probes in the study of ligand binding by recombinant soluble single chain CD1 proteins has also been evaluated, but this method is only sufficiently sensitive for the study of group I CD1 proteins. One possible reason is the binding and kinetics of association of lipid probes are too slow for detection, because all spectra were obtained immediately after combining the probes with the CD1 proteins. The fluorescent modification of the probe at the lipid tail may also affect the interaction with CD1d.

Carbohydrate microarrays allow for the rapid screening of interactions between glycans and other molecules. A quantitative glycan microarray method has been developed to determine the dissociation constants of lectins/antibodies and carbohydrate interactions at the atto-mol level. Here, a new method for the quantitative analysis of glycolipid-receptor interactions is disclosed. In this method, α-GalCer derivatives are covalently bound to a glass slide, incubated with CD1d, and their binding properties examined (e.g. dissociation constant on surface). Competition experiments, in which an intact glycolipid antigen and CD1d were mixed in solution and allowed to interact with surface α-GalCer, were used to determine the dissociation constants of new glycolipids in solution. As part of ongoing search for potent CD1d agonists, this microarray platform was used to quickly determine the dissociate constants of intact α-GalCer derivatives bearing different alkylphenyl chains at either the acyl or phytosphingosine positions.

Figure 6:
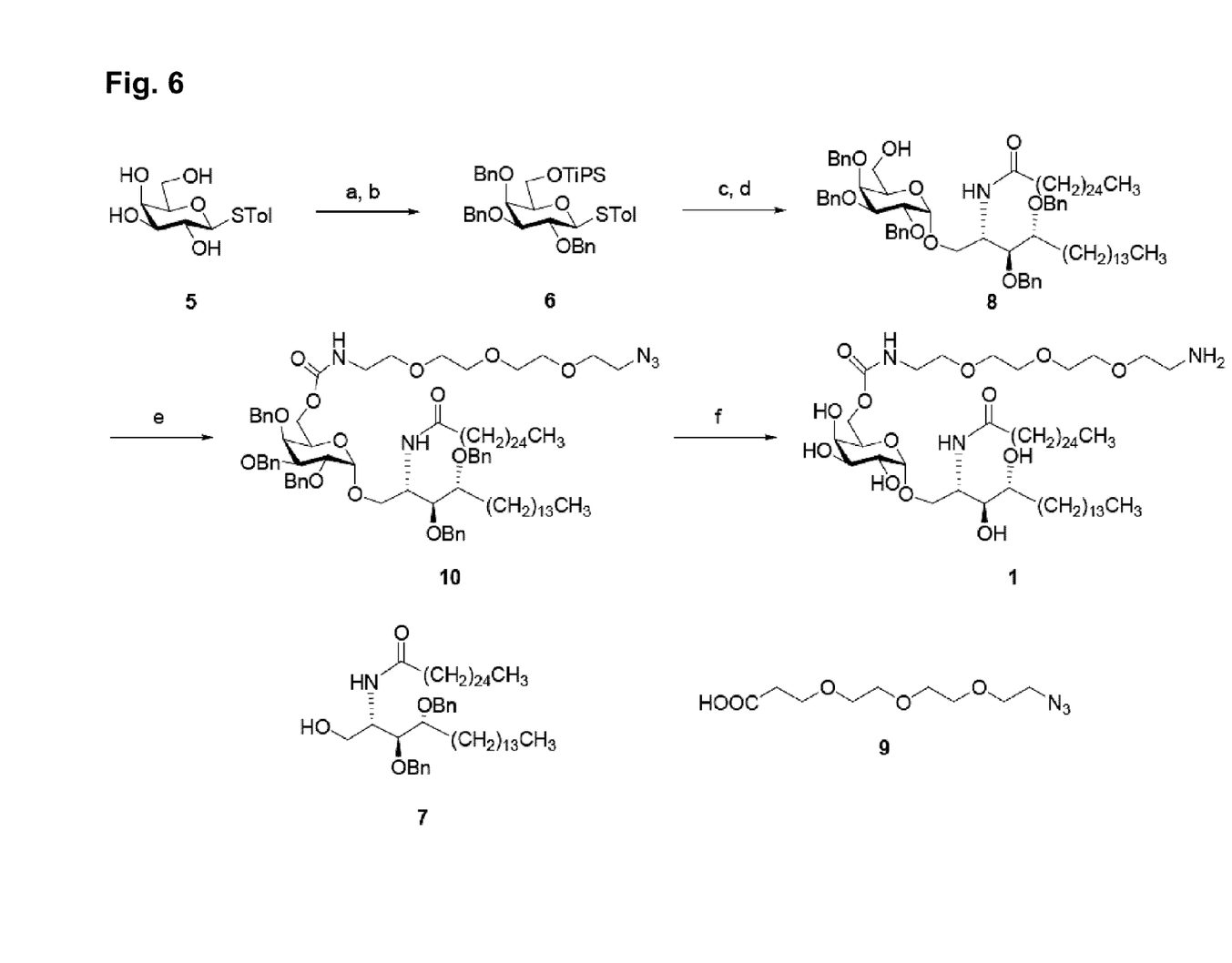
FIG. 6 shows exemplary implementations of a scheme for synthesis of compound 1. Reagents and conditions: a) TIPSCl, imidazol, THF. b) BnBr, NaH, DMF, 0° C. to rt, 55%. c) 7, BSP, Tf2O, DCM, −78° C. d) TBAF, THF, 15% (2 steps). e) 9, DPPA, $Et_3N$, Tol, reflux, 77%. f) 10% Pd/C, H2, TFA, EtOH, 95%.
Figure 7:
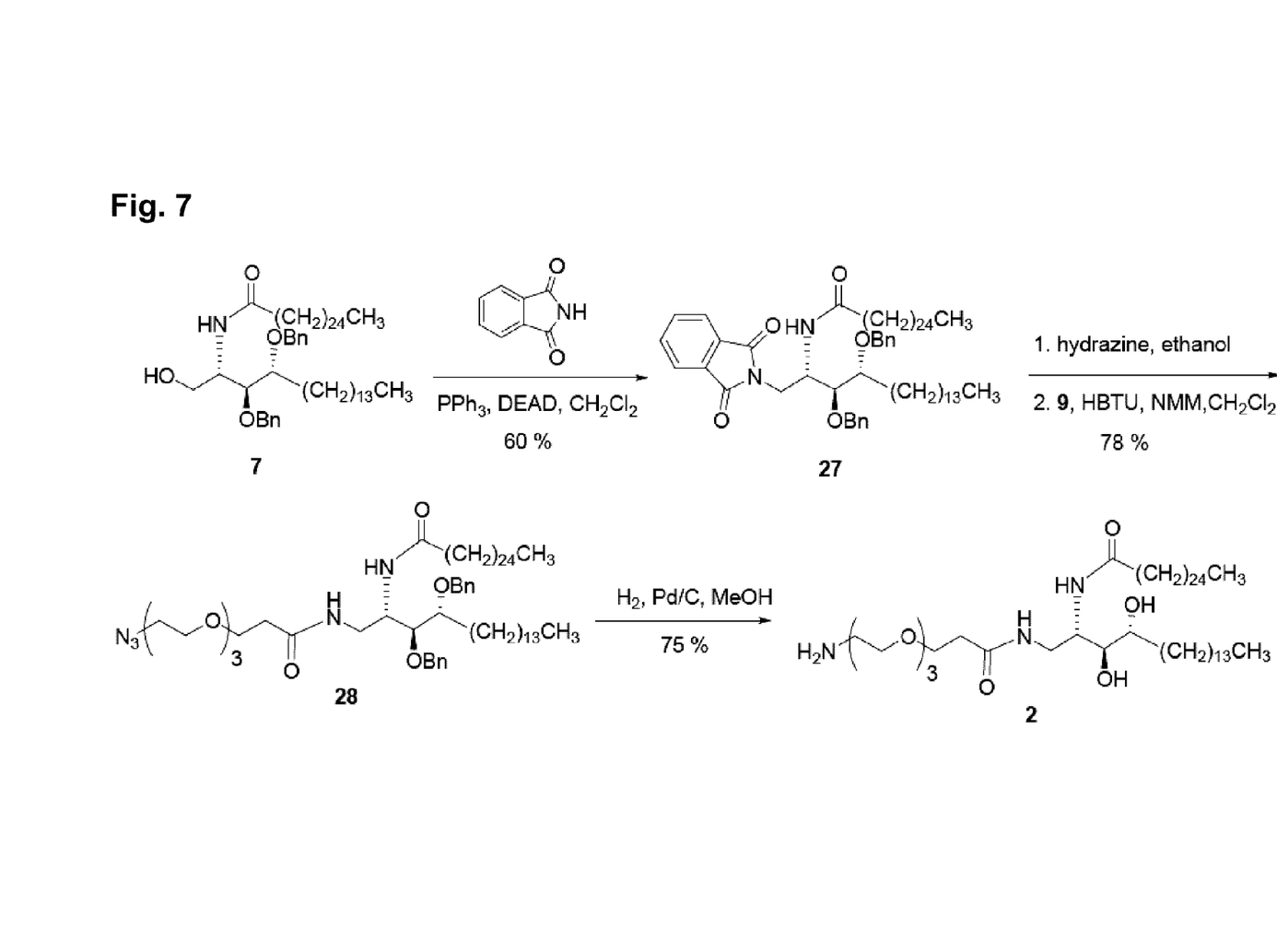
FIG. 7 shows exemplary implementations of a scheme for synthesis of compound 2.
Figure 8:
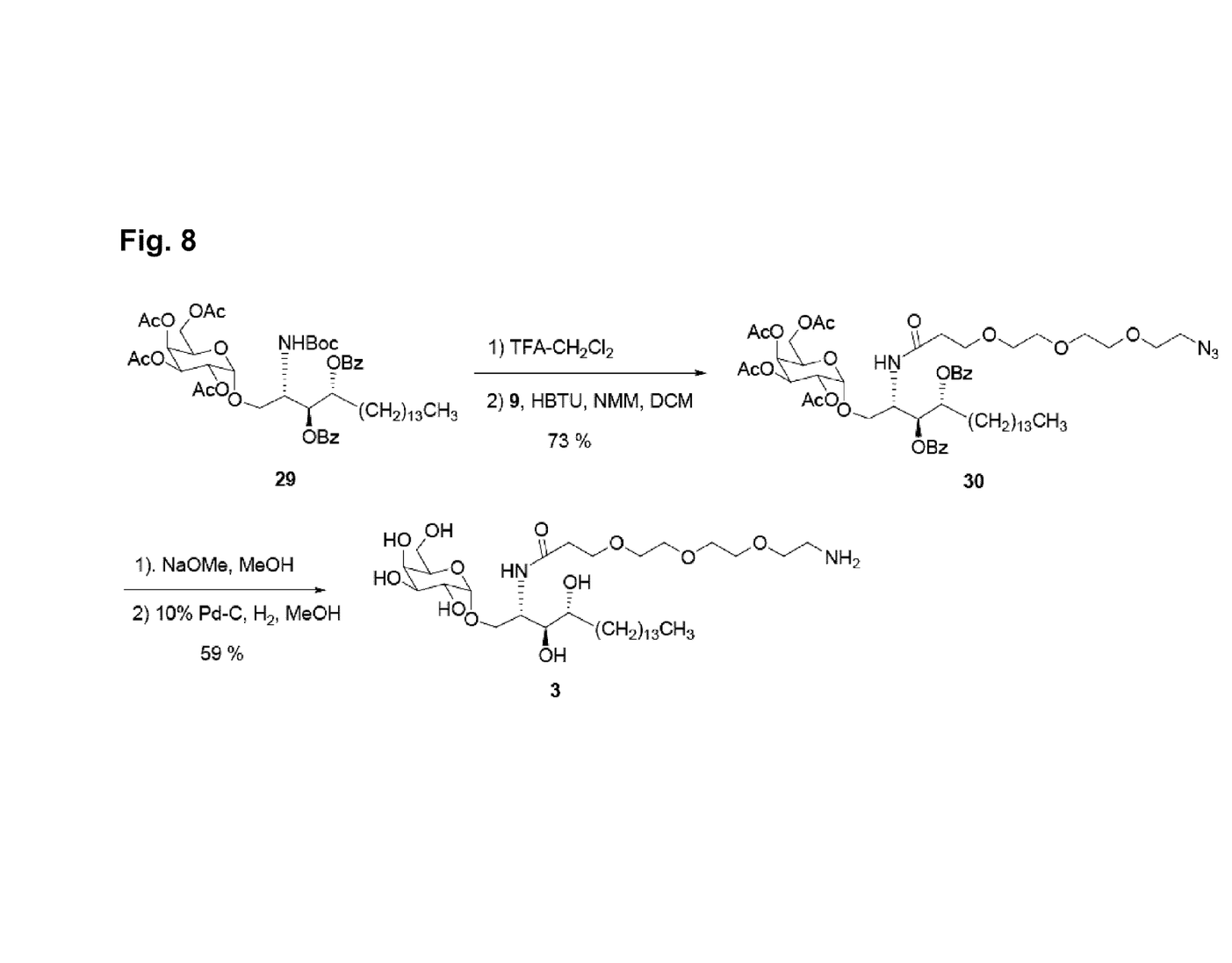
FIG. 8 shows exemplary implementations of a scheme for synthesis of compound 3.

Preparation of ligands on array surface. In order to minimize the amount of α-GalCer derivatives required for the microarray whilst maintaining a high signal/noise ratio, a ligand with higher affinity for CD1d was sought. X-ray crystallography studies showed that the 1'-anomeric O and 2'-equatorial OH of the galactose moiety and ceramide moiety with two lipid tails are essential for binding. Modification at the 6'-OH position of the sugar moiety of α-GalCer (compound 1, FIG. 1) for the attachment to the glass slide was therefore pursued. All derivatives synthesized incorporated a linker bearing a primary amine for use to attach the derivative to glass slides. In the comparative studies, compound 2 (comprising only a lipid part), compound 3 (modified at the acyl tail), and compound 4 (comprising only a galactose part), all truncated structures of α-GalCer, were used to study the binding with CD1d. Amine 1 was synthesized from thiocresol galactose (5) as shown in the scheme shown in FIG. 6. First, the hydroxyl groups of galactose 5 were protected using TIPSCl and benzyl bromide to give 6, which was glycosylated with lipid acceptor 7 in the presence of catalytic 1-benzenesulfinylpiperidine (BSP) and Tf$_2$O to afford compound 8. Silyl deprotection was achieved using TBAF/THF, and the resulting primary alcohol was coupled with isocyanate intermediate (prepared from linker 9 and diphenylphosphoryl azide (DPPA)) to afford the carbamate 10. Global deprotection of compound 10 was achieved under hydrogenolysis conditions to give compound 1. Compounds 2 and 3 were synthesized using a similar strategy (see FIGS. 7 and 8, respectively, and examples below).

Figure 2A:
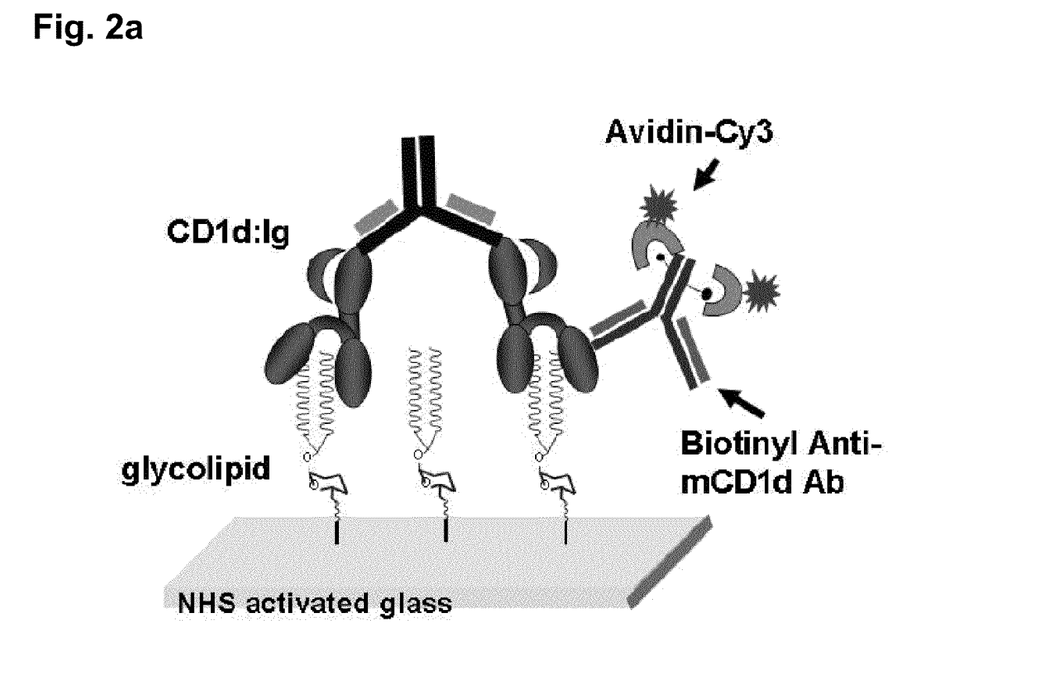
Figure 2B:
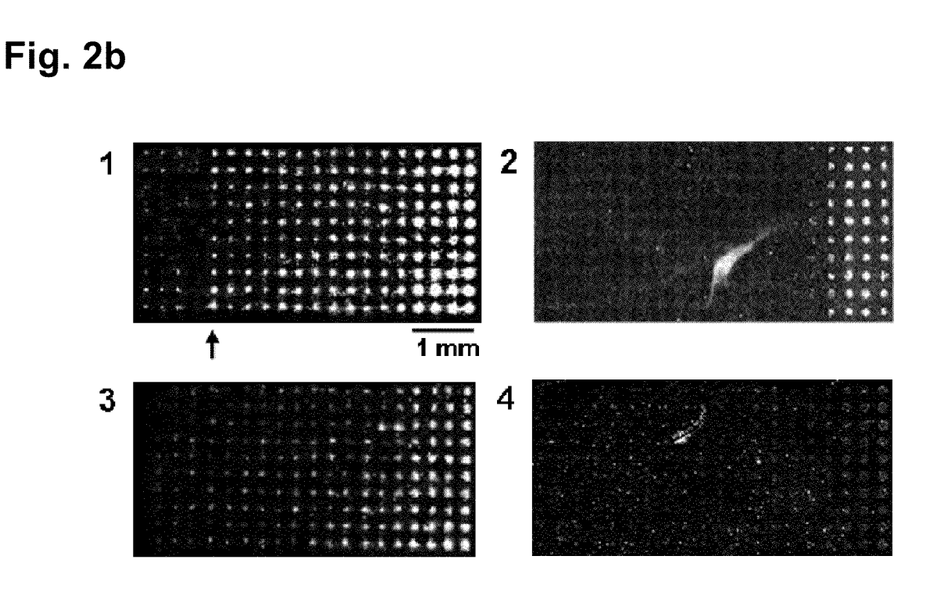

Derivatives 1-4 were printed at different concentrations (between 1 mM to 0.1 μM) on the slide coated with N-hydroxysuccinimide (NHS)-activated ester hydrogel. The binding was visualized in a two step procedure (FIG. 2a): first, commercially available recombinant dimeric mouse CD1d was bound to the surface molecules, and then detected using biotin-labeled rat anti-mCD1d antibody, pre-complex with Cy$_3$ labeled streptavidin. Compound 1 showed the best binding with CD1d, with a detection limit of 1 μM printing concentration (the lowest concentration of 1 used in the printing process); this corresponds to approximately 1 femtomole of 1 per spot (FIG. 2b). As expected, modification at the 6'-OH position of the sugar showed a less effect on binding with CD1d than modification at other positions. Compounds 2 and 3 also interacted with CD1d with low affinity. This result shows that the galactose moiety also participates in binding and that the two hydrophobic tails are necessary to fit into the two hydrophobic pockets of CD1d, consistent with the crystal studies. Compound 4 which lacked the lipid moiety did not bind with CD1d. This glycolipid-bearing, CD1d-bound array (FIG. 2a) is unique in structure as most of the previously reported microarrays (e.g. gangliosides microarray) tether the lipid moiety to the solid support and expose the sugar moiety for binding. The new glycolipid array was more sensitive than the conventional ELISA for detecting CD1d-glycolipid interaction.

Printing and incubation conditions. Optimal printing conditions were next sought. Due to the low solubility of α-GalCer in aqueous solution, 100% DMSO was used as the solvent for printing and gave the best morphology of spots. After being assayed with Cy$_3$-streptavidin, the fluorescent microspots were found to have an average diameter of 220±30 μm (n=50), about 80% larger than carbohydrates (120±20 μm, n=100) fabricated with a CMP2B pin, suggesting that there was significant spreading of lipid molecules within the microspots during the array fabrication and post-fabrication processes (FIG. 2b). The fluorescence pattern also indicates that the glycolipid is randomly and almost evenly distributed within each microspot.

In the incubation step, parameters thought to affect binding were studied: pH, detergent concentrations, DMSO concentrations, immobilization time, and lipid transporter proteins. Previous studies of the pH dependence on ligand association with CD1d proteins have yielded conflicting results. Although a number of studies showed that lipid binding to CD1d may occur preferentially in acidified endocytic compartments, in vitro studies using the surface plasmon resonance method indicated that recombinant CD1d proteins could interact with α-GalCer at neutral pH. Using compound 1, the current study confirmed the intrinsic ability of recombinant CD1d to bind ligands at neutral pH.

In addition, the effect of Tween 20, the most commonly used detergent for the binding and cell-based assays, was evaluated. Binding of CD1d with surface α-GalCer was found to be inhibited by Tween 20 at concentrations above 0.01%. Therefore, the assay was performed in 0.005% PBS buffer. Due to the low water solubility of glycolipids (less than 100 μM), the stock solutions were prepared as 1 mM (for α-GalCer) and 10 mM (other glycolipids) in DMSO solution. In the assay, DMSO was found to inhibit the binding at concentrations greater than 2.0%. In order to mitigate the influence of DMSO effects when diluting the glycolipids for assay, 1.0% DMSO was used in the assay systems.

The incubation time was also varied between one to six hours; it was found that the interaction of surface α-GalCer and CD1d reached equilibrium after 1 hour.

In vivo, glycolipids are bound to the endosomal system with lysosomal localization by lipid transfer proteins prior to delivery to CD1 proteins. Saposin B has been discovered to be the dominant saposin. To investigate the effect of saposin binding on the interactions described in this study, glycolipid 1 was incubated with various saposins (A, B, C, D) in the presence of CD1d at their preference pH (pH 5.0 for saposin A, C and pH 6.0 for saposin B, D). No significant alteration was observed.

Figure 3A:
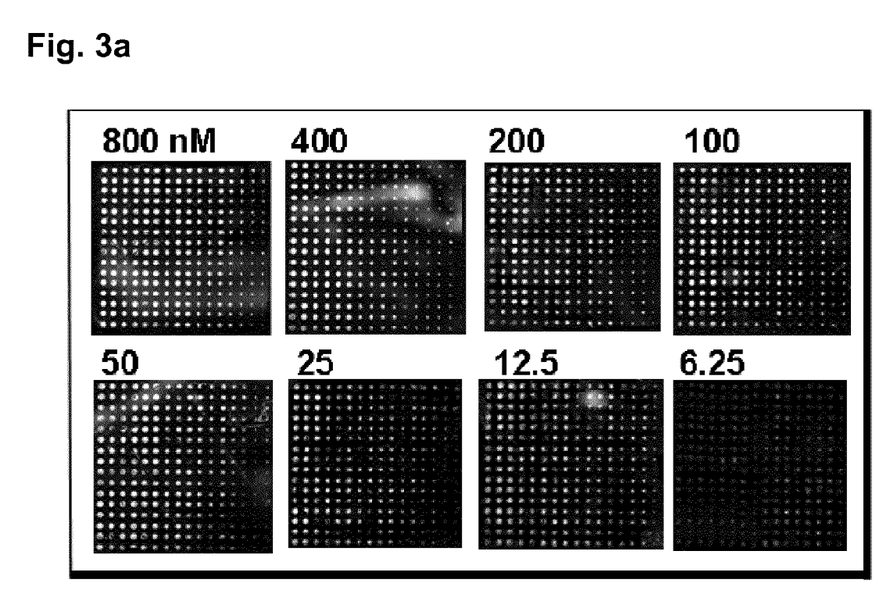
Figure 3B:
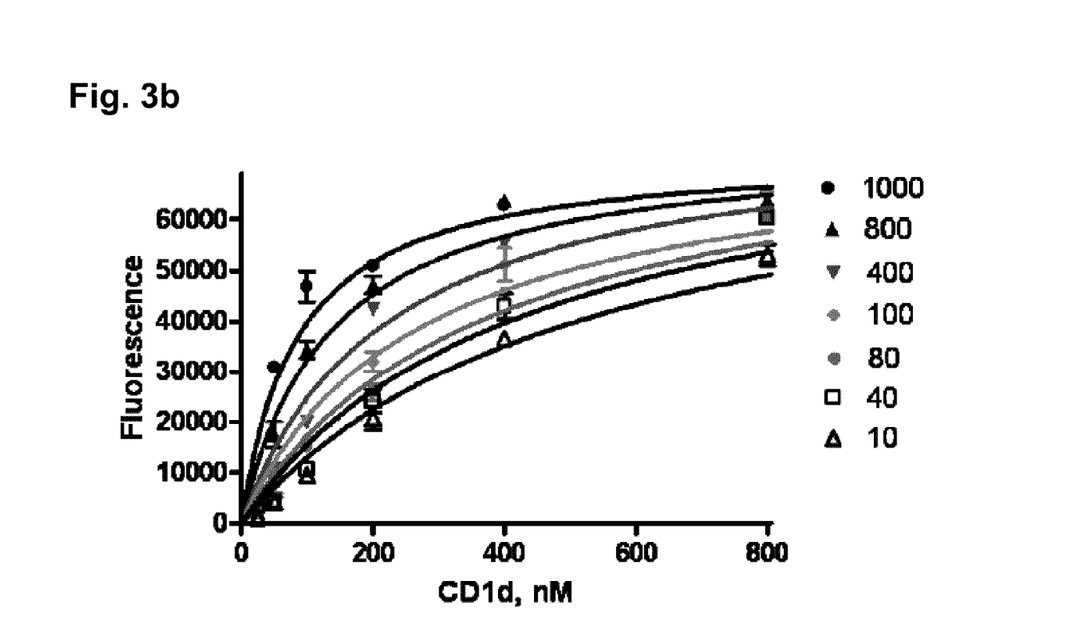

Determination of $K_{D, surf}$. To determine the dissociation constant on the surface, protein concentration was plotted against fluorescence intensity at different concentrations of compound 1 (ranging from 1 mM to 1 µM) printed on the slide. FIG. 3a depicts photographs of glass slides printed at 16 different concentrations with a 16×16 pattern of compound 1 from 1 mM (left-most column) to 5 µM (right-most column). The arrays were incubated with eight concentrations of CD1d, ranging from 800 nM to 6.25 nM. CD1d concentrations were plotted against median fluorescence intensities of replicate spots to give a set of curves for each printed concentration (FIG. 3b). Under equilibrium conditions, the curves were analyzed as Langmuir isotherms, $$F = \frac{F\max[P]}{[P] + K_{D,surf}}. \quad (1)$$

Figure 3C:
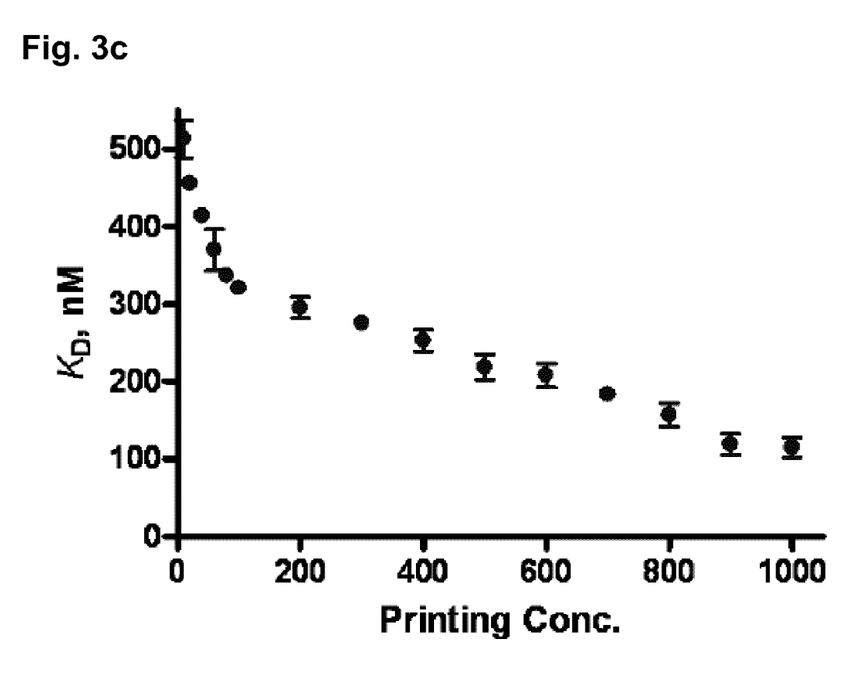

$F_{max}$ is the maximum fluorescence intensity; [P] is the total CD1d concentration; and $K_{D, surf}$ the equilibrium dissociation constant for the surface compound and CD1d. The values are plotted in FIG. 3c as a function of printing concentrations and $K_{D, surf}$. The data shows that $K_{D, surf}$ (=~100 nM at 1 mM printing concentration and =500 at 5 nM printing concentration) decreased by a factor of approximately five as the ligand density increased, reflecting tighter binding. In this assay, a 1000 µM printing concentration resulted in the highest fluorescence intensity. This was different from most glycan microarrays where the fluorescence intensities became saturated when printed at concentrations over 100 µM.

Determination of $K_i$. The solution equilibrium dissociation constant ($K_i$) for glycolipid-CD1d interactions can be determined using microarrays in a competitive assay. The equation that describes the binding of the two ligands to the same site on the protein is identical to that for the competitive inhibition of an enzyme-catalyzed reaction. It is possible to take advantage of the convenience of $IC_{50}$ measurements and still report inhibitory potency in terms of true $K_i$ values. The final forms of the relationship can be expressed as $$Ki = \frac{IC_{50}}{1 + \frac{[Po]}{K_{D,surf}}}. \quad (2)$$

In this assay, the concentration of the protein is kept constant at or near the $K_{D, surf}$ (~100-200 nM of CD1d). The glass slide is incubated with solutions containing varying concentrations of the glycolipid (covering about two orders of magnitude) and the protein. Because of the slow association and slow dissociation of CD1d with α-GalCer (demonstrated by IEF assay), the compounds were incubated with CD1d in a microtiter plate for five to eight hours prior to immobilize on glass surface.

Two types of glycolipids, the acyl modified, phenyl-alkyl chain analogs 11-25, and the phytosphingosine truncated analogs 26 were examined (FIG. 5). α-GalCer has a $K_i$ value of 14 µM, similar to the values obtained from IEF (5.9 µM) and ITC (9.7 µM). The value is 30~140 fold less than the $K_{D, surf}$ value from the interaction of CD1d with surface α-GalCer. This difference reflects the multivalent effects on the surface.

Phenylalkyl analogs 12, 13, 14 and 16 were found to bind about one order of magnitude stronger with CD1d than α-GalCer. Compounds 18-25 were intended to have different electronic properties by varying the substitutions at the para positions of heptaphenyl (18-21) and decaphenyl (22-25) Substitution with fluorine (18) was found to enhance the binding by approximately one order of magnitude, compared with parent compound 13 ($K_i$=0.14 µM). The lower binding activity of the para-Ph group (compound 21 and 25) could be due to the lack of space in the binding pocket. The phytosphingosine analog (26) was found to be a weaker agonist of mCD1d.

Figure 4:
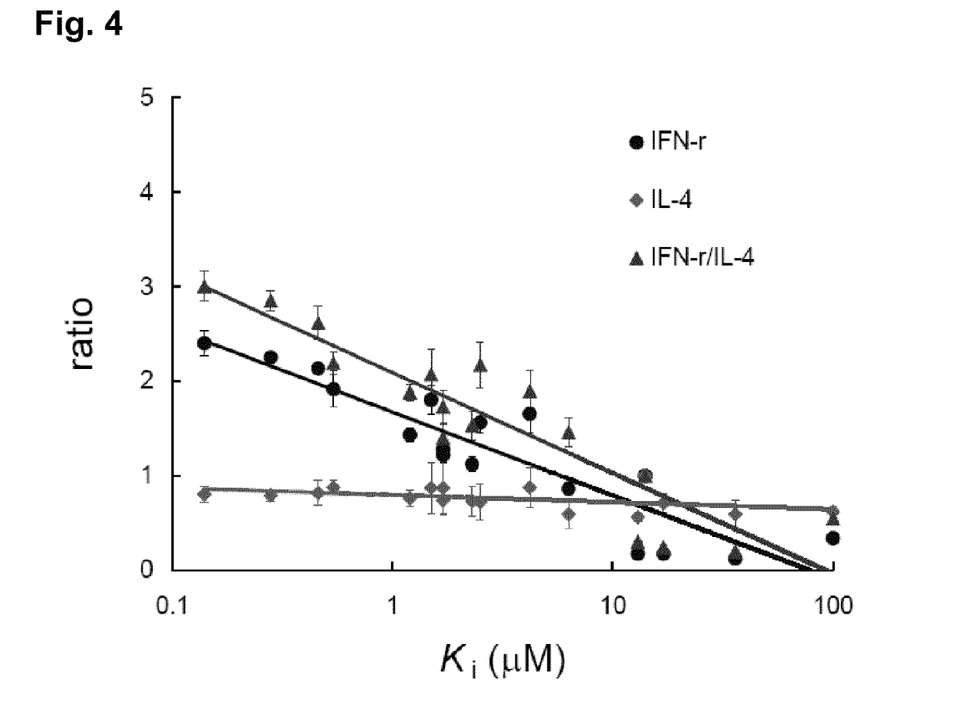
FIG. 4 illustrates exemplary implementations of plotted $K_i$ values against IFN-γ secretion, IL-4 secretion, IFN-γ/IL-4 ratios (the relationships were obtained by fitting the lines between them)
Figure 5:
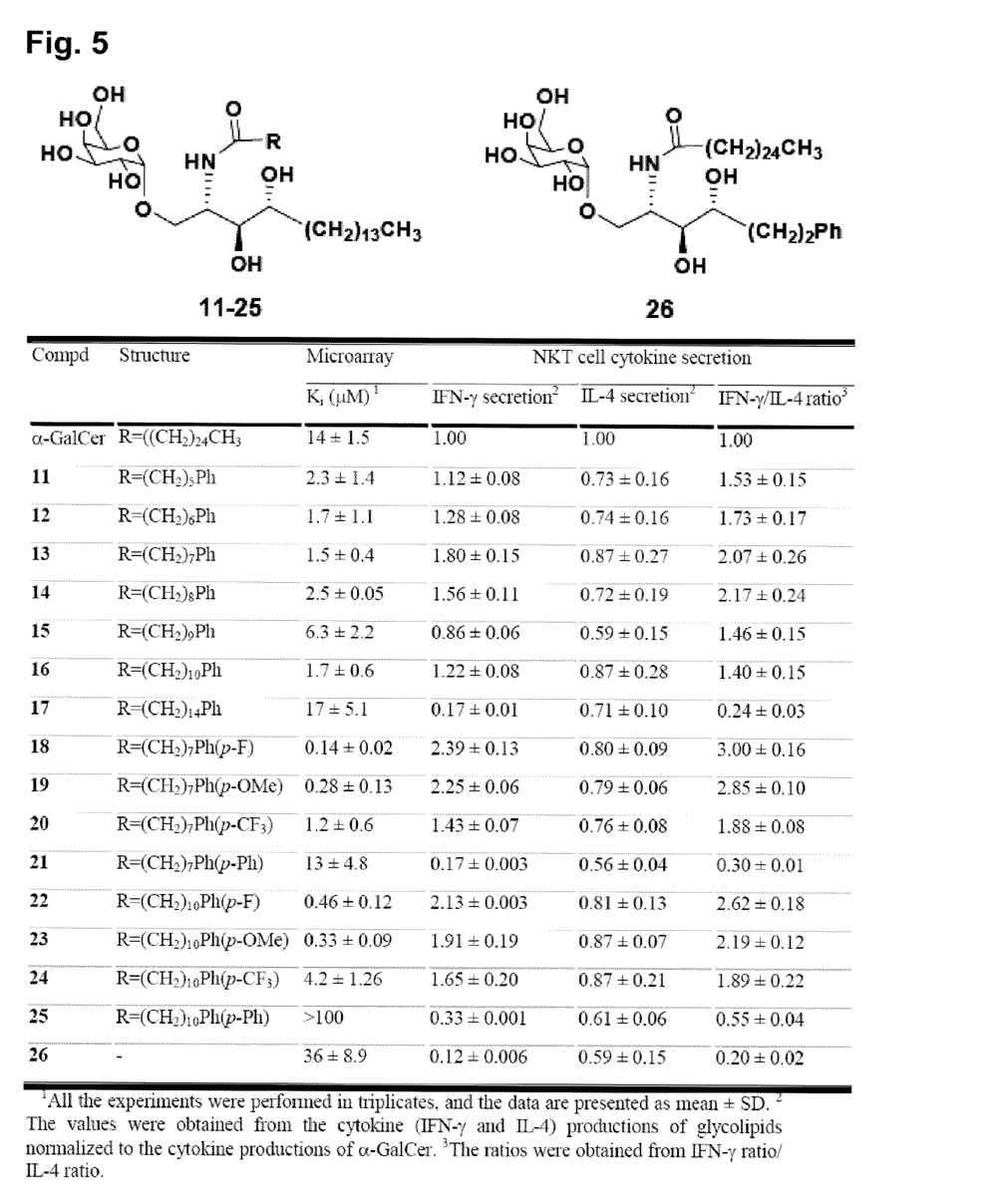
FIG. 5 shows a table demonstrating the implementations of compounds 11-25 and compound 26. The table shows the Ki (µM) values of glycolipids obtained using microarray and NKT cell-based cytokine secretions by glycolipid stimulation.

Cytokine releasing profile for new glycolipids and their correlation with array results: The ability of these glycolipids to activate human Vα24NKT cells was then evaluated by comparing their proinflammatory (INF-γ) and immunomodulatory (IL-4) responses relative to α-GalCer (FIG. 5). The glycolipids induce similar or lower level of IL-4 cytokines compared with α-GalCer. In the IFN-γ secretions, modification of the acyl chain resulted in higher production compared with α-GalCer and phytospingosine modification (26). Truncations of the phytosphingosine chain has been previously reported to diminish IFN-γ production. Compound 13, a heptaphenyl modification, had a peak IFN-γ secretions among the spacer chain elongation in acyl modification (11-17). Para-fluoro and methoxy substitutions (18, 19) resulted in the highest IFN-γ cytokine production, more than double that of the α-GalCer induced IFN-γ secretion. Values of IFN-γ secretion, IL-4 secretion, IFN-γ/IL-4 ratios were plotted against $K_i$ values and the relationships obtained by fitting lines to the data points (FIG. 4). It is interesting to note that the compounds had a trend that lower $K_i$ induced higher IFN-γ production. Those with weaker affinities to CD1d such as compounds 17, 21, and 22 induced less IFN-γ production and this resulted in a low selectivity between IFN-γ and IL-4. IFN-γ secretion and IFN-γ/IL-4 ratios correlated well with $K_i$ values with $R^2$=0.84. This observation supports the earlier assumption that compounds which had tighter binding with CD1d could bias the cytokine releasing through $T_H1$ pathway. However, almost all glycolipids, regardless of their affinity to CD1d, induce similar levels of IL-4 secretion by NKT cells— the correlation of IL-4 secretion and the binding affinity is poor ($R^2$=0.22). It was found that NKT cells are pre-activated and ready to secrete IL-4 through Notch-regulated conserved noncoding sequence-2 (CNS-2) enhancer activation. Thus, even a weak signal through their invariant TCRs can induce high level of IL-4 secretion by NKT cells.

EXAMPLE 1

Materials. NHS-coated glass slides (Nexterion H slide, SCHOTF North America), mCD1d:Ig fusion protein (BD Bioscience), biotin-labeled rat anti-mCD1d IgG2b (BD Bioscience), $Cy_3$ labeled streptavidin (Jackson ImmunoResearch), and other standard chemicals were purchased from commercial suppliers, and used as received.

EXAMPLE 2

Generation of Vα24+ human NKT cell lines. Human NKT cell lines, expressing the Vα24+ T cell receptor (TCR), were generated as follows: Vα24+ T cells and CD14+ cells were isolated from leukopaks using magnetic beads (Miltenyi biotec, Auburn, Calif.) coupled to an anti-Vα24+ TCR monoclonal antibody and an anti-CD14 monoclonal antibody, respectively. Immature dendritic cells were generated from the CD14+ cells after a three-day incubation in the presence of 300 U/ml GM-CSF (R&D systems, Minneapolis, Minn.) and 100 U/ml IL-4 (R&D systems, Minneapolis, Minn.). Following irradiation with 3000 rads, the immature dendritic cells were co-cultured with syngeneic Vα24+ T cells in the presence of 100 ng/ml of α-galactosylceramide and 10 IU/ml of IL-2 (R&D systems, Minneapolis, Minn.) for 10 days. After stimulating the Vα24+ T cells a second time with alpha-galactosylceramide-pulsed, irradiated immature dendritic cells, NKT cell lines were shown to express Vα24+ TCR (99% purity) by a flow cytometric assay.

EXAMPLE 3

Cytokine Secretion Assay using human NKT cell lines. Twenty-thousand cells of a human NKT cell line and $2 \times 10^4$ Hela cells transfected with human CD1d that had been irradiated for 10,000 rads, were co-cultured in the presence of 10 ng/ml of each glycolipid in a 96-well plate. After culture for 24 hours, the concentration of IFN-γ or IL-4 in the culture supernatants was determined by ELISA (BD Pharmingen, San Diego, Calif.).

EXAMPLE 4

Microarray Fabrication. Microarrays were printed (Genomic Solutions, Gene Machine) by robotic pin (SMP2B, TeleChem International Inc.). Approximately 0.7 mL of various concentrations of amine-containing compounds 1-4 in DMSO were deposited onto slides from a 384 well plate. The slide for: (1) the scope of printing concentration studies: NHS-coated glass slides were printed with compounds 1-4 at 20 different concentrations (1000, 800, 600, 400, 200, 100, 80, 60, 40, 20, 10, 8, 6, 4, 2, 1, 0.8, 0.6, 0.4, 0.2 μM) from right to left with 10 replicates vertically placed in each sub-array. Six identical sub-arrays were fabricated in a 1×6 pattern and each sub-array consisted of a 20×10 pattern of spots, with a 0.3 mm pitch. After 2 h, the surface of the slide was divided by permanent marker to avoid contamination for later protein incubation; (2) the slide for FIG. 2 was printed with compound 1 with concentrations of 1000 (left most column), 900, 800, 700, 600, 500, 400, 300, 200, 100, 80, 60, 40, 20, 10, 5 μM (right-most column, 16 different conc.) with 16 replicates vertically placed in each grid, and totally 16 replicate (8×2 pattern) sub-arrays in one slide; (3) the slides for $K_i$ determinations: the slides were printed of compound 1 with concentration of 1000, 900, 800 μM from right to left 81 replicates placed in each grid (9×9 pattern) and totally 44 sub-arrays replicates (4×11 pattern, each subarray is approximately 5 mm (width)×6 mm (length) area) in one slide. After 24 hours reaction, the slides were washed with PBST buffer (0.05% Tween 20) for 30 min and then blocked with blocking solution (super-block blocking buffer in PBS, Pierce) for another 1 h. The slides were dried under a flow of argon gas and stored at room temperature in a desiccator. The slides were washed with PBS buffer (pH 7.4) before use.

EXAMPLE 5

Direct Binding Assay. mCD1d:Ig fusion protein was diluted in PBS buffer and then directly applied to the sub-array of glass slides. Humidifying incubation was performed under foil for 1 hour at room temperature. The slide was following by washing procedure: (1) washed three times with incubation buffer, (2) three times with distilled water, and (3) dried with a flow of argon gas. A solution of pre-complexed rat ant-mCD1d antibody (20 μg/mL) and Cy3 labeled streptavidin (10 μg/mL) was incubated on the slide for 1 hour. The slide was again followed washing procedure and the fluorescence visualized at a resolution of 5 Å m with a 595 nm laser using an ArrayWorx microarray reader (Applied Precision).

EXAMPLE 6

Competitive Binding Assay. Solutions of the competitors at different concentration (400 to 0.1 μM) were prepared and 5 μl aliquots incubated with protein (5 μl, 100~250 nM). The mixture was then placed in a 384 well microtiter plate, covered, and left for five to eight hours. An aliquot of this solution (8 μL) was loaded onto the slides and incubated for 1 hour under a humidifying container at room temperature. The following procedure is the same as above the direct binding assay in washing procedure and applying secondary antibody. To get the data, Each inhibitor was assayed under this system at least three times and average $K_i$ values are reported.

EXAMPLE 7

Data analysis. Extraction of spot intensity data was performed using ArrayVision 8.0 (Applied Precision). The background, calculated as the median of pixel intensities from the local area around each spot, was subtracted from the mean pixel intensity within each spot. To graphically represent the data, the values of the background-subtracted signal intensities were plotted against the known concentration of the protein spotted in the array, using the commercial non-linear regression program GraphPad PRISM 4 (GraphPad, San Diego). The values obtained from the competition assay were plotted against the known concentrations of the competitors applied on the slide. The error bars indicated in the figures show the average percentage error for all data points reported in the figures. Sensitivity of detection for each spot was defined as a signal to noise ratio (S/N) of two-fold above background. S/N was calculated as: S/N=(background-subtracted median signal intensity)/(standard deviation of background signal intensity).

EXAMPLE 8

Synthesis of compound 6. Compound 6 was synthesized from compound 5 over 2 steps in the similar manner disclosed herein.

EXAMPLE 9

Synthesis of compound 8. To the stirred solution of 6 (666 mg, 0.94 mmol), 1-(benzenesulfinyl)piperidine (BSP, 147 mg, 0.70 mmol) and 2,4,6-tri-tert-butyl-pyrimidine (TFBP, 349 mg, 1.4 mmol) in 10 mL of $CH_2Cl_2$ was added $AW_{300}$ (1.0 g) and the solution was stirred for 15 min at room temperature and then added Tf2O (118 μL, 0.70 mmol) at −78° C. After 10 min, the solution was added 7 (410 mg, 0.47 mmol) in 5 mL of $CH_2Cl_2$ and then the solution was gradually heated up to 0° C. The solution was evaporated, purified by silica gel column chromatography (Hex:AcOEt 10:1) to give 260 mg of coupled product in 2:1/ratio in 38% yield. The crude product was dissolved in 5 mL of THF and added 0.2 mL of TBAF (1.0 mol/L). The solution was evaporated, purified by silica gel column chromatography (Hex:AcOEt 3:1) to afford compound 8 (91 mg, 39%) and -isomer (23 mg, 10%).

EXAMPLE 10

Synthesis of compound 10. To a stirred solution of 8 (10 mg, 0.0077 mmol) and $Et_3N$ (1 drop) in 1 mL of toluene was added DPPA (12 mg, 0.042 mmol) and refluxed for 30 min. Compound 9 (11 mg, 0.0084 mmol) was then added and refluxed over night. The solution was purified by silica gel column chromatography (Hex:AcOEt 2:1) to give compound 10 (9.2 mg) in 77% yield.

EXAMPLE 11

Synthesis of compound 1. To a stirred solution of 10 (10 mg, 0.0064 mmol) in MeOH (10 mL) was added Pd/C (20%) and 1 drop of TFA. The reaction was stirred under H2 (1 atm) for 1 day. Then, the mixture was filtered through a thick pad of Celite and the filtrate was evaporated. The residue was then purified by silical gel column chromatography (CHCl$_3$/MeOH=9/1) to give compound 1 (6.5 mg) in 95% yield.

EXAMPLE 12

Synthesis of compound 27. To a stirring solution of compound 7 (180 mg, 0.206 mmol) was added phthalimide (46 mg, 0.246 mmol), triphenylphosphine (64 mg, 0.246 mmol) and diisopropylethylamine (50 mg, 0.246 mmol) in 10 mL THF. After 1 h, the reaction mixture was evaporated and purified by silica gel column chromatography (Hex:AcOEt=6:1) to give compound 27 (124 mg) in 60% yield.

EXAMPLE 13

Synthesis of compound 28. To a stirring solution of compound 27 (120 mg, 0.119 mmol) was added hydrazine hydrate (100 μL) in ethanol (5 mL). After 2 h in room temperature, the reaction was evaporated and purified by silical gel column chromatography (CH$_3$Cl, then CHCl$_3$:MeOH=10:1) to give primary amine intermediate (76 mg) in 73% yield. The intermediate was then dissolved in CH$_2$Cl$_2$ (10 mL) and added HBTU (66 mg, 0.174 mmol), acid 9 (24 mg, 0.096 mmol) and N-methylmorpholine (26 mg, 0.26 mmol). After stirring at room temperature for 12 h, the mixture was evaporated and purified by silical gel column chromatography (Hex:AcOEt=1:1, then AcOEt) to give compound 28 (102 mg) in 78% yield.

EXAMPLE 14

Synthesis of compound 2. To a solution of compound 28 (75 mg, 0.067 mmol) was added Pd/C (10 mg) and a drop of TFA in methanol (15 mL) under 1 H2 (1 atm). After stirring at room temperature for 1 day, the mixture was filtered through a thick pad of Celite and the filtrate was evaporated. The mixture was then purified by silical gel column chromatography (CHCl$_3$:MeOH=9:1) to give compound 2 (50 mg) in 75% yield.

EXAMPLE 15

Synthesis of compound 30: To a solution of compound 29 (50 mg, 0.053 mmol) was added a solution of TFA:CH$_2$Cl$_2$=1:1 (6 mL) at 0° C. After 6 h, the reaction mixture was evaporated and dried by pump. The residue was added acid 9 (14 mg, 0.053 mmol), HBTU (30 mg, 0.079 mmol), and NMM (2 mL) in THF (5 mL). After stirring at room temperature for 1 day, the mixture was evaporated and purified by silical gel chromatography (Hex:AcOEt=2:1, then 1:1) to give 30 (42 mg) in 73% yield.

EXAMPLE 16

Synthesis of compound 3. To a solution of compound 30 (40 mg, 0.037 mmol) was added sodium methoxide (1.0 N solution in MeOH). The resulting solution was stirred at room temperature for 1 h and was neutralized by adding Dowex (H+). The mixture was filtered and the filtrate was evaporated to give the intermediate. Then, the intermediate was added MeOH (10 mL), Pd/C (10%, 5 mg), 1 drop of TFA and H2 (1 atm). After stirring at room temperature for 1 day, the mixture was filtered through a thin pad of Celite and the filtrate was evaporated and dried by pump to give compound 3 (15 mg) in 59% yield in two steps.

EXAMPLE 17

A-4, Synthesis of compound 12, 14-15, 17-22. General procedures to synthesize fatty acyl chain analogues and phytospingosine analogues may be in accordance with implementations disclosed herein.

While the apparatus and method have been described in terms of what are presently considered to be the most practical and exemplary implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A device comprising:
a plurality of glycan ligands bound to a substrate via a linker bearing a primary amine group suitable for attachment to the substrate, the linker group attached at a derivatized 6'—OH position of the sugar moiety of α-GalCer;
wherein the glycan ligands are α-Galactosylceramide (α-GalCer) derivatives of Formula 1:

(1)

wherein R is CHR$_1$—X—Y;
R1 is an organic moiety such as selected from the group consisting of amide, carbamate, carbonate, and urea;
X is alkyl, alkoxyl, or aryl-alkyl; and
Y is NH$_2$, COOH, N$_3$, alkyne, or biotin.

2. The device of claim 1, wherein the device comprises a microarray.

3. The device of claim 1, wherein the substrate is a glass slide.

4. A method comprising:
(a) providing a device according to claim 1;
(b) incubating the device with CD1 molecules; and
(c) taking measurements to determine binding of the CD1 molecules to the α-GalCer derivatives of Formula 1.

5. The method of claim 4, wherein the measurements comprise determining a dissociation constant of the CD1 molecules with the α-GalCer derivatives of Formula 1.

6. The method of claim 4, wherein the incubating step further comprises glycolipid antigens.

* * * * *